United States Patent [19]

Rombusch et al.

[11] Patent Number: 4,582,941

[45] Date of Patent: Apr. 15, 1986

[54] PROCESS FOR PRODUCING SQUARIC ACID

[75] Inventors: Konrad Rombusch; Gunther Maahs, both of Marl, Fed. Rep. of Germany

[73] Assignee: Huels Aktiengesellschaft, Marl, Fed. Rep. of Germany

[21] Appl. No.: 600,969

[22] Filed: Apr. 16, 1984

[30] Foreign Application Priority Data

Apr. 21, 1983 [DE] Fed. Rep. of Germany ....... 3314431

[51] Int. Cl.$^4$ .............................................. C07C 45/00
[52] U.S. Cl. .................................................... 568/364
[58] Field of Search ........................................ 568/364

[56] References Cited

U.S. PATENT DOCUMENTS

| | | | |
|---|---|---|---|
| 2,650,939 | 9/1953 | McBee et al. | 568/364 |
| 3,169,147 | 2/1965 | Blomquist et al. | 568/364 |
| 4,097,530 | 6/1978 | Schroeder et al. | 568/364 |
| 4,104,308 | 8/1978 | Gadek et al. | 568/364 |
| 4,272,633 | 6/1981 | Maahs et al. | 568/364 |

FOREIGN PATENT DOCUMENTS 2824558 12/1979 Fed. Rep. of Germany ...... 568/364

Primary Examiner—James H. Reamer
Attorney, Agent, or Firm—Millen & White

[57] ABSTRACT

A process for producing squaric acid comprises reacting hexachlorocyclobutene, or its mixtures with hexachlorobutadiene, with 96–100% sulfuric acid, at 80°–150° C., and adding at least the stoichiometric amount of water required for the hydrolysis, while maintaining the acid concentration between 96% and 100% throughout the reaction.

12 Claims, No Drawings

PROCESS FOR PRODUCING SQUARIC ACID

BACKGROUND OF THE INVENTION

The present invention relates to an improved process for producing squaric acid.

Squaric acid (quadratic acid; 1,2-dihydroxy-3,4-cyclobutenedione) is a valuable intermediate product for the manufacture of stabilizers, dyes, bactericides, and fungicides. A number of processes for its preparation are known, as described in detail in U.S. Pat. No. 4,097,530. According to the method disclosed in the aforementioned patent, squaric acid is prepared by reaction of hexachlorocyclobutene with 70–96% by weight sulfuric acid at temperatures of between 80° and 150° C. The best results are achieved by reacting hexachlorocyclobutene with 90% by weight sulfuric acid at 120° C. In this process, 4–10 hours are required to react hexachlorocyclobutene to form squaric acid, and, in general, another 3 hours are needed to drive the reaction to completion and to evaporate the proportion of the resultant hydrogen chloride that has remained dissolved in the reaction mixture.

By raising the reaction temperature from 120° C. to, for example, 140° C., the required reaction period can be reduced, as expected, but in that case, tars are generated which discolor the squaric acid (Example 7). The reference discloses that, if the sulfuric acid concentration deviates markedly from the optimum value of 90% by weight in the downward as well as upward directions, so that it is outside the range 70–96%, the reaction is unsuccessful. Only small amounts of squaric acid are formed below a sulfuric acid concentration of 70% by weight, even with the use of higher temperatures and pressures. Above a sulfuric acid concentration of 96% weight, there is almost no hydrolysis because of the low amount of water present (column 2, lines 8–16).

The above-mentioned patent describes the possibility of adding water (Example 5) or dilute sulfuric acid (Example 3 of the reference) during the reaction, or initially using adequate amounts of 90% strength sulfuric acid, in order to maintain an optimum water concentration. Also, in the examples of the reference, the sulfuric acid concentration during the entire reaction is maintained well below 96% by weight in all cases.

Thus, the teaching of this reference is to start with a sulfuric acid concentration of not more than 96% and to avoid permitting the acid concentration to rise above 96% at any time during the reaction. Water is added to keep the acid concentration below 96%. There is no recognition that it might be advantageous to start the reaction at a sulfuric acid concentration above 96% and to maintain the acid at a concentration above 96% during the entire course of the reaction. Rather, this is directly contrary to the teaching of this reference and to the entire thrust of its disclosure.

Although the above-described process also permits use of mixtures of hexachlorocyclobutene with hexachlorobutadiene, Example 4 of the reference demonstrates that reaction of a mixture of 50% each of hexachlorocyclobutene and hexachlorobutadiene results in a yield that is reduced with respect to the optimum by 20%, at 120° C., and the product is only obtained after a reaction time of 15 hours. Such results are unacceptable for industrial processes. Furthermore, the reaction product becomes colored after such a long reaction period. Mixtures wherein the hexachlorocyclobutene proportion is even lower are hardly usable at all.

On the other hand, great interest exists, for economic and industrial reasons, in being able to utilize mixtures having as low a proportion of hexachlorocyclobutene as possible. As is known, such mixtures can be produced more cheaply because of lower distillation costs (see German Patent 2,618,557). Solutions of such a low percentage have the further advantage in handling that the point of crystallization of the cyclic isomer is so low as to prevent it from precipitating from the solution at room temperature.

German Patent 2,824,558 describes another process for the preparation of squaric acid wherein hexachlorocyclobutene or its mixture with hexachlorobutadiene is initially heated with oleum (fuming sulfuric acid, i.e., containing at least 10 mole % $SO_3$ in 100% $H_2SO_4$) to 60°–120° C. and subsequently, in a second process step, in the reaction mixture, the organic intermediate is hydrolyzed to squaric acid and the thus-formed chlorosulfonic acid is hydrolyzed to sulfuric acid.

Apart from the fact that industrial use of oleum is best avoided, for financial reasons and on account of its aggressive and toxic effects, this process has additional drawbacks. Special precautions are necessary to hydrolyze the chlorosulfonic acid formed during the reaction. An unexpected and troublesome occurrence during the reaction is the formation of products that are extremely lachrymatory. Under these circumstances, realization of the process under industrial conditions is fraught with considerable technical and toxicological difficulties.

German Patent 2,824,558 does not contain any suggestion of operating with oleum having a low $SO_3$ concentration, (i.e., less than 10 mole % $SO_3$, because in such a case the quantity of sulfuric acid would have to be significantly increased.

A need therefore continues to exist for a process for the production of squaric acid which avoids these disadvantages.

OBJECTS OF THE INVENTION

One object of the present invention is to provide a process for producing squaric acid which permits use of mixtures of hexachlorocyclobutene and hexachloro-1,3-butadiene, especially those wherein the proportion of the cyclic isomer is below 55%.

Another object of the invention is to provide a process wherein the reaction periods are shorter than indicated in U.S. Pat. No. 4,097,530, and wherein the temperature can be set at such a low point that there is no formation of colored final products.

A further object is to provide a process which permits recovery of sulfuric acid employed, and which can be conducted on an industrial scale without toxicological problems.

Upon further study of the specification and appended claims, further objects and advantages of this invention will become apparent to those skilled in the art.

SUMMARY OF THE INVENTION

These objectives can be attained by a process for producing squaric acid, comprising the steps of reacting hexachlorocyclobutene with sulfuric acid having a concentration of more than 96% by weight, at a temperature of 80°–150° C., and adding at least the stoichiometric amount of water required to hydrolyze the hexachlorocyclobutene to squaric acid, while maintaining the acid concentration above 96% throughout the reaction; and recovering resultant squaric acid.

DETAILED DESCRIPTION

The present process is based on the surprising finding that the reaction rate in the claimed range does not decrease with a drop in water concentration but, on the contrary, considerably increases if only the stoichiometrically required amount of water is provided. This discovery is not only in contradiction to the data in U.S. Pat. No. 4,097,530, it is also contradictory to the customary assumption of a proportionality between reaction rate and concentration of reactants.

The overall hydrolysis reaction effects the following conversion:

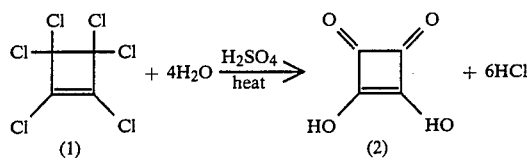

It is necessary during the course of the hydrolysis reaction to provide 4 moles of water per mole of hexachlorocyclobutene (1) converted to squaric acid (2).

In the process according to the present invention, the initial concentration of the sulfuric acid is more than 96% by weight, i.e., the water content of the acid, with respect to the sum total of sulfuric acid and water, is not more than 4% preferably less than 4%, i.e., not more than 3.9% (at least 96.1% $H_2SO_4$); more preferably, the acid strength is higher than 96.5%, e.g., at least 96.6%; still more preferably, the acid strength is higher than 98%, e.g., at least 98.1%. Advantageously, the acid strength during the reaction is below 100%, at least after the initial evolution of hydrogen chloride, e.g., not higher than 99.95%, preferably 99.8%. A convenient range is about 97-98% acid strength during the major part of the reaction.

Water or dilute $H_2SO_4$, e.g., 10-30% $H_2SO_4$, is added during the course of the reaction to maintain the acid concentration between 96% and 100% and to replace the water consumed in the hydrolysis reaction. Normally, the water or dilute $H_2SO_4$ is added in a metered fashion to maintain the acid strength at or above its initial value, but in any case within the critical range between 96% and 100%. Continuous monitoring and adjustment of the acid can be effected by conventional means, e.g., by titration of resultant hydrogen chloride gas evolved in the reaction, which is related to the extent of reaction, and attendant consumption of water, according to the foregoing reaction scheme.

Alternatively, it is possible to start with 100% sulfuric acid and to add water or dilute $H_2SO_4$ in metered amounts after the reaction has started, advantageously after the initial evolution of hydrogen chloride has subsided, e.g., after about 2 moles of hydrogen chloride per mole of hexachlorocyclobutene have evolved, to furnish water for hydrolysis, the water content of the acid being kept below 4%, e.g., 0.05-3.9% (96.1-99.95% acid).

The reaction is carried out at a temperature of 80°-150° C., preferably 110°-135° C.; normally at ambient pressure. The range from 120° to 125° C. is especially advantageous because the reaction rate here is adequate and the formation of tars is still very minor, so that the resultant crude product is substantially colorless. At a temperature below 80° C., the reaction rate is undesirably low. Above 150° C., excessive tars are formed. Additionally, at such high temperatures, thermal rearrangement of hexachlorocyclobutene to hexachlorobutadiene is initiated, the latter compound being unreactive in the reaction medium.

The hexachlorocyclobutene can be added to the sulfuric acid in a single portion at the beginning of the reaction or in incremental portions at the beginning and during the further course of the reaction, for example after splitting off specific percentages of the hydrogen chloride to be removed by cleavage.

Mixtures of hexachlorocyclobutene and hexachlorobutadiene can be used as the starting material for the process of the invention, including mixtures having a proportion of the cyclic isomer below 55%, e.g., about 50%, 45%, and even as low as about 20 %. The hexachlorobutadiene is substantially unreactive under the conditions of the present process and can be removed by conventional procedures, e.g., as disclosed in U.S. Pat. No. 4,097,530. Mixtures containing minor 10% hexachlorocyclobutene are disadvantageous for economical reasons.

The amount of sulfuric acid employed depends, as mentioned above, on the particular variant of the process chosen. It is most advantageous to use, per mole of hexachlorocyclobutene, 6-14 moles of sulfuric acid, of which more than 90% can be recovered. If the sulfuric acid is not to be reused, water is added to the reaction mixture until the sulfuric acid has reached a concentration of 65-75%, and the reaction mixture is cooled, which causes the squaric acid to precipitate. The resultant crude product is separated, e.g., by filtration, optionally washed with, e.g., cold water and/or petroleum ether, and dried. Further purification can be effected by conventional means, e.g., crystallization. The crude product, which normally has a purity of at least about 95 %, preferably at least 97%, is suitable for some industrial uses without further purification.

On the other hand, if the sulfuric acid is required for a subsequent reaction batch, the reaction mixture is cooled to between about 20° C. and about 10° C., after termination of hydrogen chloride evolution. The reaction product crystallizes out and can be removed by filtration, hexachlorobutadiene in the filtrate can be separated if necessary, and the remaining sulfuric acid can be immediately introduced into the next reaction. The low losses of sulfuric acid obtained in this way can be readily compensated for by adding fresh acid.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following example(s), all temperatures are set forth uncorrected in degrees Celsius; unless otherwise indicated, all parts and percentages are by weight.

The 0.1N $KMnO_4$ solution utilized to determine the content of squaric acid was calibrated on a sample recrystallized four times with water. This sample showed potentiometrically a content of squaric acid of 99.75%, a water content of 0.06%, a Cl content of 0.003%, and an S content of 0.0003%.

EXAMPLE 1

Under agitation (blade agitator, 350 rpm), a mixture of 129.6 g (0.497 mol) of hexachlorocyclobutene, 132.2 g (0.507 mol) of hexachlorobutadiene, and 663 g of 96.2% by weight sulfuric acid (6.56 mol) was heated in a 1-liter glass flask to 122° C. The split-off hydrogen chloride was absorbed in a receiver filled with 15% strength sodium hydroxide solution, and the thus-absorbed quantity was determined by titrimetry. After absorption of about 0.05–0.25 mol of hydrogen chloride, the quantity of water consumed by the hydrolysis reaction, i.e., 35.8 g of water, was added in metered amounts so that the water concentration in the sulfuric acid was 2.0–3.8% by weight, based on the sum total of sulfuric acid and water. After 3.5 hours, 2.7 mol of hydrogen chloride had been split off, 25% thereof after 0.48 hour, 50% after 0.87 hour, 75% after 1.32 hours, and 95% after 2.54 hours. After termination of the reaction, 330 g of water was added to the reaction solution and the latter was cooled off. The thus-precipitated squaric acid was suctioned off, washed three times with respectively 15 cc of water, then with 200 cc of petroleum ether, and then dried, thus obtaining 53.9 g of a crude product. The potassium permanganate titration showed a yield of 88.3%.

EXAMPLE 2

In a 1-liter glass flask, a mixture of 130.6 g (0.501 mol) of hexachlorocyclobutene, 130.4 g (0.50 mol) of hexachlorobutadiene, and 650 g of 99.8% by weight sulfuric acid (6.61 mol) was heated to 125° C. under agitation (blade agitator, 350 rpm). The split-off hydrogen chloride was absorbed in a receiver filled with 15% sodium hydroxide solution, and the thus-absorbed amount was determined by titrimetry. After absorption of about 0.05–0.25 mol of hydrogen chloride, the quantity of water consumed by the hydrolysis reaction, i.e. 36 g of water, was added in doses so that the water concentration in the sulfuric acid was 0.2–0.4% by weight, based on the sum total of sulfuric acid and water. After termination of the reaction, 345 g of water was added to the reaction mixture. After cooling, the thus-precipitated squaric acid was suctioned off, washed three times with 15 cc portions of water, then with 200 cc of petroleum ether, and thereafter dried, thus obtaining 51.4 g of a crude product. Potassium permanganate titration showed a yield of 83.3%.

EXAMPLE 3

Under agitation (blade agitator, 350 rpm), a mixture of 104.3 g (0.400 mol) of hexachlorocyclobutene, 104.6 g (0.401 mol) of hexachlorobutadiene, and 533.8 g of 97.0% by weight sulfuric acid (5.28 mol) was heated in a 1-liter glass flask to 135° C. The split-off hydrogen chloride was absorbed in a receiver filled with 15% sodium hydroxide solution, and the absorbed amount was determined by titrimetry. After absorption of about 0.05–0.25 mol of hydrogen chloride, the quantity of water consumed by the hydrolysis reaction, i.e. 2.9 g of water, was added in metered amounts so that the water concentration in the sulfuric acid was 1.7–3.0% by weight, based on the sum total of sulfuric acid and water. After termination of the reaction, 260 g of water was added to the reaction mixture. After cooling, the thus-precipitated squaric acid was suctioned off, washed three times with 15 cc portions of water, then with 200 cc of petroleum ether, and thereafter dried, thus producing 41.0 g of a crude product. Potassium permanganate titration showed a yield of 86.2%.

EXAMPLE 4

In a 1-liter glass flask, a mixture of 32.7 g (0.125 mol) of hexachlorocyclobutene, 33.3 g (0.128 mol) of hexachlorobutadiene, and 664.2 g of 97.0% by weight sulfuric acid (6.57 mol) was heated to 120° C. under agitation (blade stirrer, 350 rpm). The thus-split-off hydrogen chloride was absorbed in a receiver filled with 15% strength sodium hydroxide solution, and the absorbed amount was determined titrimetrically. After absorption of about 0.05–0.25 mol of hydrogen chloride, the amount of water consumed by the hydrolysis reaction, i.e. 9 g of water, was added in metered quantities so that the water concentration in the sulfuric acid was 2.0–3.5% by weight, based on the sum total of sulfuric acid and water. After 0.06 mol of HCl had been split off (this was after 0.1 hour), a mixture of 32.4 g (0.124 mol) of hexachlorocyclobutene and 32.9 g (0.126 mol) of hexachlorobutadiene was added; after another 0.86 mol of HCl had been split off (which was after 0.77 hour), a mixture of 64.8 g (0.249 mol) of hexachlorocyclobutene and 65.9 g (0.253 mol) of hexachlorobutadiene was added, and after splitting off another 1.19 mol of HCl (this was after 1.75 hours), a mixture was added made up of 77.9 g (0.299 mol) of hexachlorocyclobutene and 79.1 g (0.303 mol) of hexachlorobutadiene. After completion of the reaction, 330 g of water was admixed to the reaction mixture. After cooling, the thus-precipitated squaric acid was suctioned off, washed three times with 15 cc portions of water, then with 200 cc of petroleum ether, and then dried, thus obtaining 84.2 g of a crude product. Potassium permanganate titration gave a yield of 87.1%.

EXAMPLE 5

Under agitation (blade agitator, 350 rpm), a mixture of 43.3 g (0.166 mol) of hexachlorocyclobutene, 0.7 g (0.003 mol) of hexachlorobutadiene, and 215 g of 100% by weight sulfuric acid (2.19 mol) was heated in a 1-liter glass flask for 0.75 hour to 125° C. The split-off hydrogen chloride was absorbed in a receiver filled with 15% strength sodium hydroxide solution, and the absorbed amount was determined by titrimetry. Subsequently, within one hour at 115° C., 21.0 g of water was added dropwise to the reaction mixture and further stirred for one hour at the same temperature. During this step, another 0.56 mol of hydrogen chloride was split off. The reaction solution was combined with 110 g of water. After cooling, the thus-precipitated squaric acid was suctioned off, washed three times with 15 cc portions of water, then with 200 cc of petroleum ether, and then dried, thus producing 18.2 g of a crude product. Potassium permanganate titration showed a yield of 91.6%.

EXAMPLE 6

In a 1-liter glass flask, a mixture of 130.0 g (0.50 mol) of hexachlorocyclobutene, 130.0 g (0.50 mol) of hexachlorobutadiene, and 414.1 g of 97.1% by weight sulfuric acid (4.1 mol) was heated under agitation to 120° C. The split-off hydrogen chloride was absorbed in a receiver filled with 15% strength sodium hydroxide solution, and the absorbed amount was determined by titrimetry. After absorption of about 0.05–0.25 mol of hydrogen chloride, the amount of water consumed by the hydrolysis reaction was added in metered quantities in such a way that the water concentration in the sulfuric acid was 2.0–3.0% by weight, based on the sum total of sulfuric acid and water. After cooling to 0° C., the thus-precipitated squaric acid was suctioned off, washed three times with 15 cc portions of water then with 200 cc of petroleum ether, and then dried, thus isolating 44.2 g of product. Potassium permanganate titration showed a yield of 72.4%.

The organic phase of the remaining filtrate was separated, and the loss of acid was compensated for by adding 21 g of 97% strength sulfuric acid. Thereupon the sulfuric acid was heated a second time in a 1-liter glass flask under agitation together with a mixture of 130.0 g (0.50 mol) of hexachlorocyclobutene, 130.0 g (0.50 mol) of hexachlorobutadiene to 120° C. The split-off hydrogen chloride was absorbed in a receiver filled with 15% sodium hydroxide solution, and the absorbed quantity was determined titrimetrically. After absorption of respectively 0.05 to 0.25 mol of hydrogen chloride, the amount of water consumed by the hydrolysis reaction was added in metered amounts so that the water concentration in the sulfuric acid was 2.0 to 3.0% by weight, based on the sum total of sulfuric acid and water. After cooling to 0° C., the thus-precipitated squaric acid was suctioned off, washed three times with 15 ml portions of water, thereafter with 200 ml of petroleum ether, and then dried. Potassium permanganate titration showed a yield of 84.8%. The filtrate was worked up in the same way as described above, and used twice more. Then it was discarded.

EXAMPLE 7

In a 1-liter glass flask, a mixture of 104.3 g (0.400 mol) of hexachlorocyclobutene, 243.3 g (0.933 mol) of hexachlorobutadiene, and 533.8 g of 97.0% by weight sulfuric acid (5.28 mol) was heated under agitation (blade agitator, 350 rpm) to 123° C. The split-off hydrogen chloride was absorbed in a receiver filled with 15% strength sodium hydroxide solution, and the amount absorbed was determined by titrimetry. After absorption of about 0.05–0.25 mol of hydrogen chloride, the amount of water consumed by the hydrolysis reaction was added in metered quantities so that the water concentration in the sulfuric acid was 2.0–3.0% by weight, based on the sum total of sulfuric acid and water. After termination of the reaction, 230 g of water was added to the reaction mixture. After cooling, the thus-precipitated squaric acid was suctioned off, washed three times with 15 cc portions of water, then with 200 cc of petroleum ether, and thereafter dried, thus obtaining 39.8 g of a crude product. Potassium permanganate titration gave a yield of 84.1%

EXAMPLE 8

In a 1-liter glass flask, a mixture of 104.3 g (0.40 mol) of hexachlorocyclobutene, 104 3 g (0.40 mol) of hexachlorobutadiene, and 266.9 g of 97.0% by weight sulfuric acid (2.64 mol) was heated to 125° C. under agitation (blade agitator, 350 rpm). The hydrogen chloride that was split off was absorbed in a receiver filled with 15% strength sodium hydroxide solution, and the absorbed quantity was determined by titrimetry. After absorption of about 0.1–0.5 mol of hydrogen chloride per mol of hexachlorocyclobutene employed, the quantity of water consumed by the hydrolysis reaction, i.e. 4 mol of water per 6 mol of hydrogen chloride, was added in metered amounts so that the water concentration in the sulfuric acid was 2.1–3.2% by weight, based on the sum total of sulfuric acid and water. After 6.0 hours, 2.10 mol of hydrogen chloride had been split off, 25% thereof after 0.63 hour, 50% after 1.15 hours, 75% after 2.03 hours, and 95% after 3.80 hours. After termination of the reaction, 130 g of water was added to the reaction mixture. After cooling, the thus-precipitated squaric acid was suctioned off, washed three times with 15 cc portions of water, with 250 cc of petroleum ether, and then dried, thus obtaining 36.8 g of a crude product. Potassium permanganate titration showed a yield of 84.1%.

EXAMPLE 9

Under agitation (blade stirrer, 350 rpm), a mixture of 129.7 g (0.497 mol) of hexachlorocyclobutene, 3.1 g (0.012 mol) of hexachlorobutadiene, and 667.3 g of 97.0% by weight sulfuric acid (6.6 mol) was heated to 120° C. in a 1-liter glass flask. The split-off hydrogen chloride was absorbed in a receiver filled with 15% sodium hydroxide solution, and the absorbed amount was determined titrimetrically. After absorption of about 0.1–0.5 mol of hydrogen chloride per mol of hexachlorocyclobutene utilized, the amount of water consumed by the hydrolysis reaction was added in metered quantities so that the water concentration in the sulfuric acid was 2.0–3.3% by weight, based on the sum total of sulfuric acid and water. After 2.25 hours, 2.70 mol of hydrogen chloride had been split off, 25% thereof after 0.28 hour, 50% after 0.49 hour, 75% after 0.69 hour, and 95% after 0.95 hour. After termination of the reaction, 320 g of water was added to the reaction mixture. After cooling, the thus-precipitated squaric acid was removed by suctioning, washed three times with 15 cc portions of water, with 200 cc of petroleum ether, and then dried, thus yielding 52.3 g of a crude product. Potassium permanganate titration gave a yield of 87.7%.

EXAMPLE 10

In a 1-liter glass flask, a mixture of 149.9 g (0.575 mol) of hexachlorocyclobutene, 149.2 g (0.572 mol) of hexachlorobutadiene, and 743 g of 100% by weight sulfuric acid (7.58 mol) was heated for 1.5 hours to 120°–125° C. under agitation (blade agitator, 350 rpm). The split-off hydrogen chloride was absorbed in a receiver filled with 15% sodium hydroxide solution, and the absorbed amount was determined by titrimetry: 1.04 mol. Subsequently, 72.4 g of water was added dropwise to the reaction mixture within one hour at 120°–125° C., and the mixture was further stirred for 0.75 hour at the same temperature, thus splitting off another 2.21 mol of hydrogen chloride. The reaction solution was combined with 370 g of water. After cooling, the thus-precipitated squaric acid was suctioned off, washed three times with 15 cc portions of water, with 200 cc of petroleum ether, and then dried, thus obtaining 59.3 g of a crude product. Potassium permanganate titration showed a yield of 83.7%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for producing squaric acid, comprising the steps of reacting a mixture comprising hexachloro-1,3-butadiene and about 20-55% of hexachlorocyclobutene with sulfuric acid having a concentration of between 96.5% and 100% by weight, at a temperature of 80°-150° C., and adding at least the stoichiometric amount of water required to hydrolyze the hexachlorocyclobutene to squaric acid, while, maintaining the acid concentration between 96.5% and 100% throughout the reaction, thereby increasing the rate of the hydrolysis reaction compared to that obtained with lower acid concentrations.

2. The process of claim 1, wherein said concentration of said sulfuric acid is about 97-98%.

3. The process of claim 1, wherein the initial concentration of the sulfuric acid is 100%; and water or dilute sulfuric acid is added after the initial evolution of hydrogen chloride has subsided, to adjust and maintain the acid strength between 96.5% and 99.95%.

4. The process of claim 1, wherein said reaction temperature is 110°-135° C.

5. The process of claim 4, wherein said temperature is 120°-125° C.

6. The process of claim 1, of said hexachlorocyclobutene wherein said proportion is 30-50%.

7. The process of claim 1, wherein the amount of sulfuric acid used is 6-14 moles per mole of hexachlorocyclobutene.

8. The process of claim 1, wherein the resultant squaric acid is recovered by cooling the reaction mixture to about 0°-20° C., and separately recovering resultant crude crystalline squaric acid, and a filtrate of sulfuric acid.

9. The process of claim 8, wherein said recovered sulfuric acid is thereafter reacted with fresh hexachlorocyclobutene.

10. The process of claim 1, wherein the resultant squaric acid is recovered by adding water to the reaction mixture until the sulfuric acid is diluted to about 65-75%, cooling the mixture and separating resultant crystalline squaric acid.

11. The process of claim 5, wherein the resultant squaric acid is substantially colorless.

12. The process of claim 1, wherein the resultant squaric acid has a purity of at least 95%.

* * * * *